(12) United States Patent
Kew et al.

(10) Patent No.: US 9,402,709 B2
(45) Date of Patent: Aug. 2, 2016

(54) COLLAGEN GEL FOR BONDING POROUS COLLAGEN-BASED MATERIALS WITH NON-POROUS COLLAGEN-BASED MATERIALS

(75) Inventors: Simon Kew, Cambridgeshire (GB); Tim Mead, Cambridgeshire (GB); Neil Rushton, Cambridgeshire (GB)

(73) Assignee: Tigenix Limited, Cambridge (GB)

( * ) Notice: Subject to any disclaimer, the term of this patent is extended or adjusted under 35 U.S.C. 154(b) by 881 days.

(21) Appl. No.: 13/582,795

(22) PCT Filed: Mar. 7, 2011

(86) PCT No.: PCT/GB2011/050439
§ 371 (c)(1),
(2), (4) Date: Apr. 17, 2013

(87) PCT Pub. No.: WO2011/107807
PCT Pub. Date: Sep. 9, 2011

(65) Prior Publication Data
US 2013/0197662 A1    Aug. 1, 2013

(30) Foreign Application Priority Data
Mar. 5, 2010   (GB) .................................. 1003656.4

(51) Int. Cl.
*A61L 15/32* (2006.01)
*A61L 31/12* (2006.01)
*A61F 2/02* (2006.01)
(Continued)

(52) U.S. Cl.
CPC . *A61F 2/02* (2013.01); *A61L 27/24* (2013.01); *A61L 27/26* (2013.01); *A61L 27/46* (2013.01); *A61L 27/52* (2013.01); *A61L 31/044* (2013.01);
(Continued)

(58) Field of Classification Search
None
See application file for complete search history.

(56) References Cited

U.S. PATENT DOCUMENTS

| 5,171,273 A | 12/1992 | Silver et al. |
| 5,282,859 A * | 2/1994 | Eisenberg ............... A61F 2/105 128/DIG. 8 |

(Continued)

FOREIGN PATENT DOCUMENTS

| WO | 9321857 | 11/1993 |
| WO | 2005051447 A1 | 6/2005 |

(Continued)

OTHER PUBLICATIONS

International Search Report for Int'l Application No. PCT/GB2011/050439, filed Mar. 7, 2011.

(Continued)

*Primary Examiner* — Jeffrey E Russel
(74) *Attorney, Agent, or Firm* — Harness, Dickey & Pierce, PLC

(57) ABSTRACT

The invention discloses a process for fabricating a biomaterial, comprising: a) joining a porous collagen based-material with a non-porous collagen based-material by applying a controlled amount of a bonding layer of a gel comprising collagen to a bonding surface of the non-porous collagen based-material, and contacting a surface of the porous collagen based-material with the gel applied to the bonding surface to partially hydrate a section of the porous material at the interface between the materials; b) drying the gel to dry to bond the materials together; and c) cross-linking the collagens in the bonding layer. Also disclosed are biomaterials and implants produced using the fabrication process.

23 Claims, 8 Drawing Sheets

Figure 1:
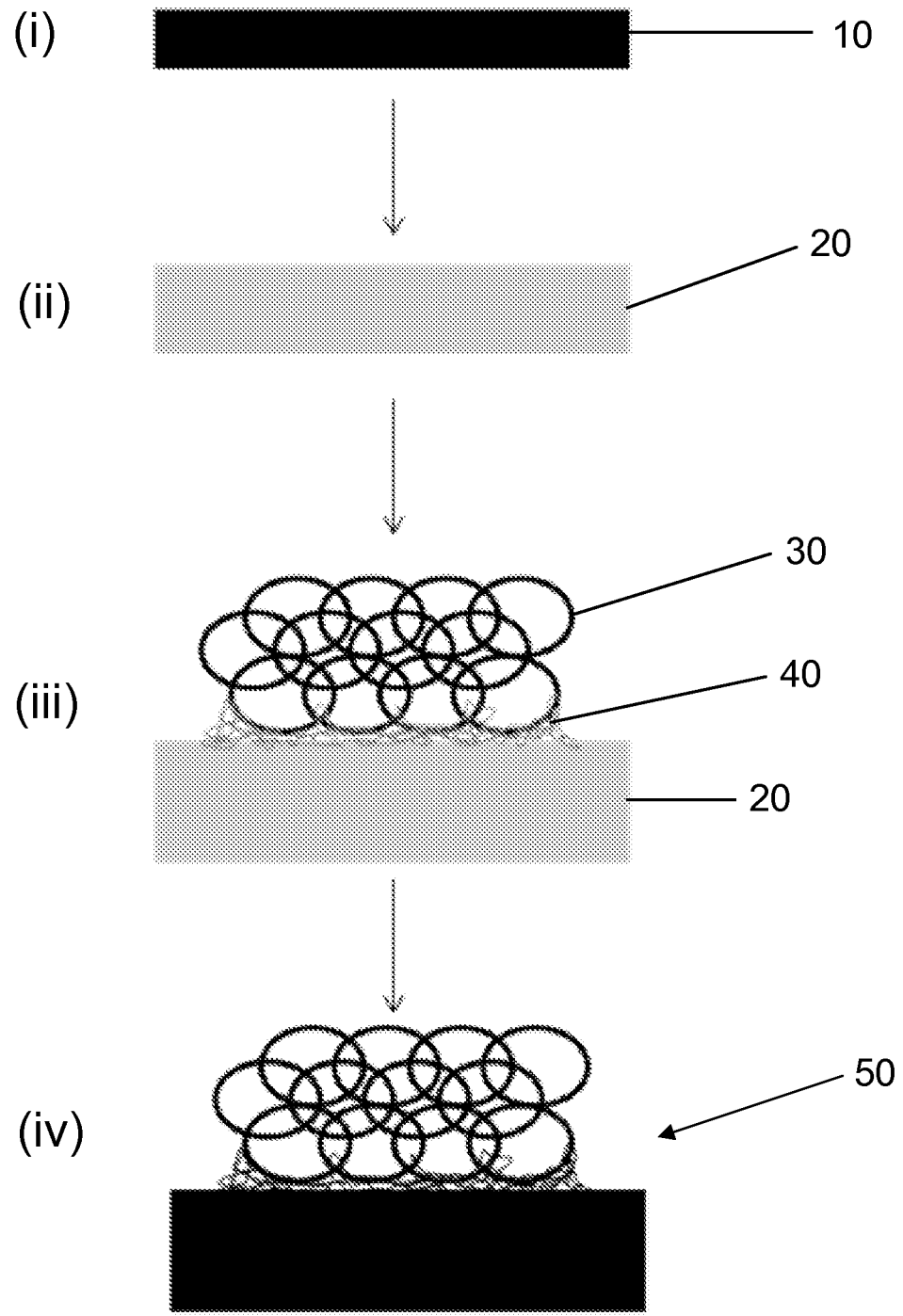

(51) Int. Cl.
*A61L 31/04* (2006.01)
*A61L 27/24* (2006.01)
*A61L 27/26* (2006.01)
*A61L 27/46* (2006.01)
*A61L 27/52* (2006.01)
*C09J 189/06* (2006.01)
*A61F 13/00* (2006.01)

(52) U.S. Cl.
CPC ...... *C09J 189/06* (2013.01); *A61F 2013/00357* (2013.01); *A61L 2400/18* (2013.01)

(56) References Cited

U.S. PATENT DOCUMENTS

| | | | | |
|---|---|---|---|---|
| 8,865,215 | B2* | 10/2014 | Ladet | A61L 27/48 424/485 |
| 9,272,073 | B2* | 3/2016 | Ladet | A61L 27/48 |
| 2007/0198059 | A1* | 8/2007 | Patel | A61B 17/0057 606/213 |
| 2008/0295735 | A1 | 12/2008 | Ragaru et al. | |
| 2010/0016872 | A1* | 1/2010 | Bayon | A61F 2/0063 606/151 |
| 2010/0248368 | A1* | 9/2010 | Lynn | A61L 27/46 435/404 |

FOREIGN PATENT DOCUMENTS

| | | |
|---|---|---|
| WO | 2006095154 A2 | 9/2006 |
| WO | 2008017858 A2 | 2/2008 |

OTHER PUBLICATIONS

Curtis D. Chin et al: "A microfabricated porous collagen-based scaffold as prototype for skin substitutes", Biomedical Microdevices, Kluwer Academic Publishers, BO, vol. 10, No. 3, Jan. 23, 2008, pp. 459-467, XP019600451, ISSN: 1572-8781 the whole document.

Amir A. Al-Munajjed et al: "Influence of pore size on tensile strength, permeability and porosity of hyaluronan-collagen scaffolds", Journal of Materials Science: Materials in Medicine, Kluwer Academic Publishers, BO, vol. 19, No. 8, Mar. 18, 2008, pp. 2859-2864, XP019607881, ISSN: 1573-4838 the whole document.

* cited by examiner

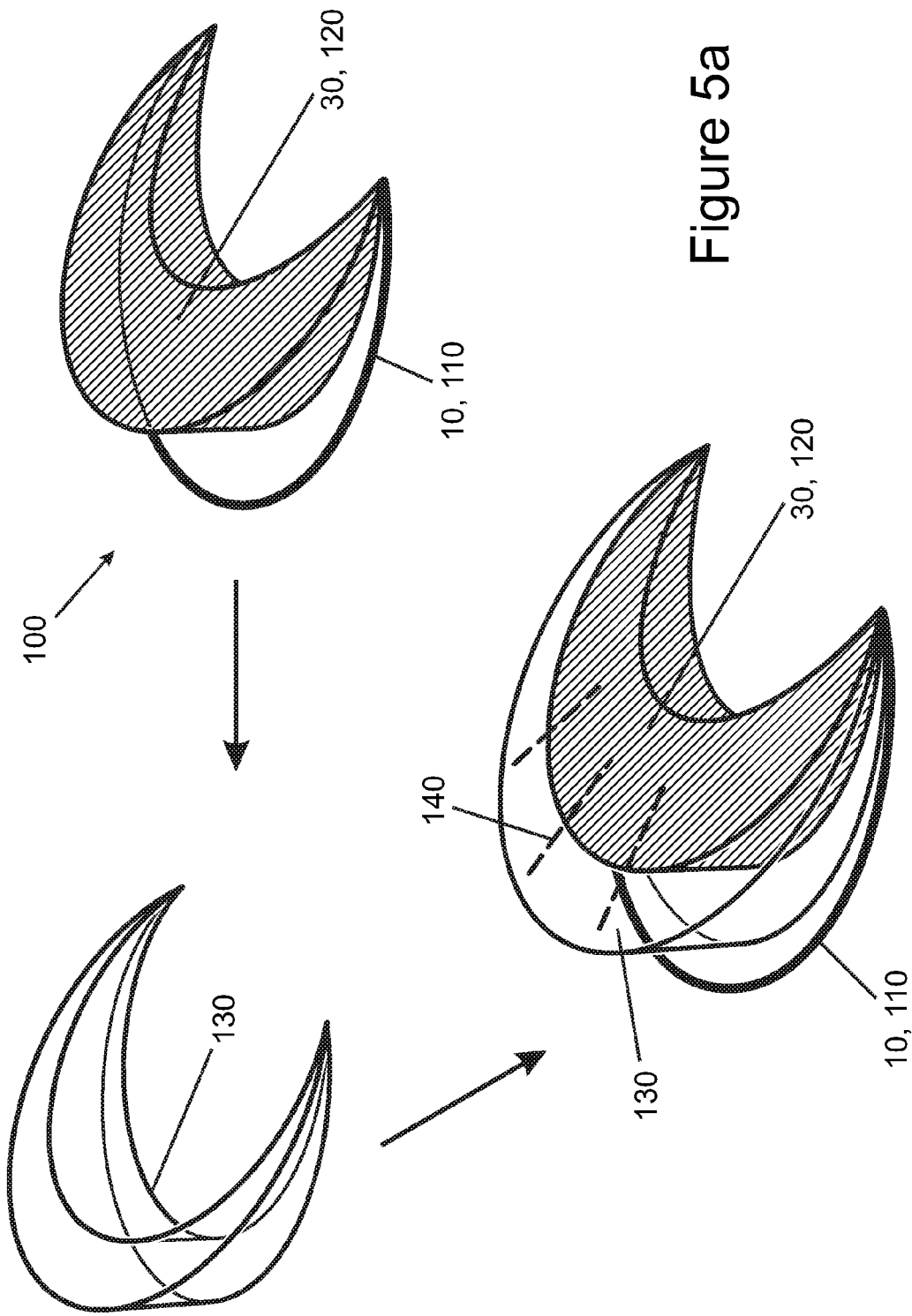

COLLAGEN GEL FOR BONDING POROUS COLLAGEN-BASED MATERIALS WITH NON-POROUS COLLAGEN-BASED MATERIALS

CROSS-REFERENCE TO RELATED APPLICATIONS

This application is a 371 U.S. National Stage of International Application No. PCT/GB11/050439, filed on Mar. 7, 2011, and claims priority to British Patent Application No. 1003656.4, filed on Mar. 5, 2010, the disclosures of which are herein incorporated by reference in their entirety.

The present invention relates to a method for fabrication of biomaterials that can be used as tissue regeneration scaffolds in clinical applications requiring the repair of damaged tissues. Specifically, the invention relates to a new fabrication process for joining porous and non-porous biomaterials to create new biomaterial formats having both porosity and mechanical strength.

Porous collagen-based biomaterials are commonly used as scaffolds for the repair and regeneration of damaged tissues, utilising their porous structure to enable cellular growth, proliferation, migration and infiltration into a defect site. Whilst porous collagen-based biomaterials are limited by substantial mechanical weakening caused by the existence of pores in the material, these pores are necessary in order to promote cellular proliferation and infiltration during the degradation process following implantation thus allowing the material to mediate (i.e. provide a scaffold for) the regeneration of damaged tissues. The inherent mechanical weakness of porous materials means (i) they cannot be fixed or anchored in place using conventional fixation techniques such as suturing and (ii) they cannot be used to mimic or repair load bearing tissues which have inherent mechanical strength, for example tendons and ligaments. Furthermore, their porosity limits their ability to be used to contain biological species such as biomolecules or cells which may be utilised for pharmacological effect. Collagen scaffolds have traditionally been limited to being either porous but weak structures or dense but strong structures.

Combining a porous collagen-based material with a mechanically strong non-porous collagen-based material potentially provides scaffolds for regeneration of tissues where both mechanical strength and porosity are required. There are several applications for orthopaedic repair and in dental medicine where the ability to combine these materials into a single structure would be advantageous.

The bone-soft tissue interface is difficult to regenerate using biomaterials which provide a scaffolding matrix for the development of new tissue due to the structural differences between the different tissue types. The ideal scaffold for this application would be capable of directing the regeneration of isotropic tissues requiring extensive vascularisation (e.g. cancellous bone) and mimicking avascular tissues, such as tendon, ligament and fibrocartilage, where mechanical strength in an orientation is more important. A suitable scaffold would require a combination of different materials types because porous materials, particularly those composed of collagen, have inadequate mechanical properties for load bearing applications and furthermore are not aligned.

U.S. Pat. No. 5,171,273 discloses processes for fabricating biocompatible collagen grafts having high tensile strength.

EP0639959 B1 discloses a prosthetic ligament manufactured by braiding cross-linked low density collagen filaments with high density filaments.

Combination of porous and non-porous collagen-based materials enables the production of a material that can provide a substantially permeable and a substantially impermeable compartment. Thus this material structure is designed to provide the capability to sequester and selectively deliver biologically relevant species such as cells and biomolecules to tissue defect sites. The ability to fabricate biomaterials with both a permeable and an impermeable compartment is also required in applications where the delivery of a therapeutic agent such as cells or proteins is required without premature loss of such agents via diffusion or hydrodynamic flow, such as that found in a synovial joint. The current state of the art for the combination of porous and non-porous materials for filling defects in sites relevant to orthopaedic and dental medicine involves the use of separate porous and non porous components. For example, dental tooth extraction sockets can be filled using a porous bone void filler and are then isolated using a substantially impermeable membrane. It would be advantageous to use a contiguous biomaterial having both porous and non-porous properties.

It is known to use collagen in glues to join biomaterials together because it is capable of solidifying and then being reabsorbed, and it is biocompatible. Collagen as such, however, has weak adhesive power. US 2008/0295735 discloses a glue comprising a mixture of collagen and a cross-linking agent of the aldehyde type or a modified collagen with aldehyde functions and presented in lyophilised form.

Whilst combining porous collagen-based materials (with low mechanical strength) and non-porous collagen-based materials (with high mechanical strength) would provide new and advantageous biomaterial formats, the main problem with fabricating "hybrid" collagen-based biomaterials (i.e. those having porosity and mechanical strength) is that the components are not readily integrated, and do not bond well because known glues are weak and invariably require a chemical cross-linking treatment which can result in the creation of cytotoxic by-products. The present invention seeks to overcome the problems associated with prior art methods and materials by providing a method to fabricate a biomaterial that provides the functionality of both porous and non-porous materials in a single contiguous material, thus enabling porosity to be combined with mechanical strength.

According to a first aspect of the present invention, there is provided a process for fabricating a biomaterial, comprising
a) joining a porous collagen based-material with a non-porous collagen based-material by applying a controlled amount of a bonding layer of a gel comprising collagen to a bonding surface of the non-porous collagen based-material, and contacting a surface of the porous collagen based-material with the gel applied to the bonding surface to partially hydrate a section of the porous material at the interface between the materials;
b) drying the gel to dry to bond the materials together; and
c) cross-linking the collagens in the bonding layer.

The term "biomaterial" as used herein means a material that is biocompatible with a human or animal body. The term "porous" as used herein means that the material may contain macropores and/or micropores. The fabricated biomaterial of the invention is defined as contiguous because previously separate non-porous and porous collagen-based materials lie adjacent each together after fabrication. The fabricated biomaterial is also defined as continuous, because the collagens in the respective porous and non-porous materials are bonded to the collagen in the bonding layer of gel at one or more interfaces to create a bonded and integrated biomaterial having the functionality and properties of each of the component materials.

In order to assemble a fixed spatial configuration of porous and non-porous materials it has been identified that dispensing controlled amounts of a gel comprising collagen may be used to bond the materials together. Collagen gels are commonly used to form cast structures however, their use in methods to bond porous and non-porous materials has not been achieved to date. Use of inadequate or excessive amounts of collagen gel to adhere the materials results in several deleterious effects on the fabricated biomaterial. The ability to adhere the materials using a controlled way in which to dispense the collagen gel is key to the assembly of the collagen materials used within the process. The joining step is preferably carefully controlled in order to ensure that the porosity of the porous collagen-based material is not compromised when the gel is applied. The joining step and the quality of the resulting bond may be controlled by using a controlled amount of gel with a known viscosity. A controlled amount of gel is defined as the amount which is sufficient to only partially hydrate a section of the porous collagen-based material at the planned interface between the porous and non-porous materials. The applicant has determined that porous and non-porous collagen-based materials can be bonded using a bonding layer of between 50-100 µm in thickness. The amount of collagen gel applied in the bonding layer may be between 50-500 µL cm$^{-2}$. If the amount of collagen gel used is too high, the porosity of the porous component is compromised by the capillary uptake of collagen gel into the porous component. Applying too much gel thus over-hydrates the porous collagen-based material, eliminating the pore structure and damaging the quality of the biomaterial produced using the process. Conversely, using too little gel results in insufficient infiltration of the gel into the porous collagen based-material, providing an incomplete bond, resulting in insufficient adhesion between the materials and leading to gaps being present between the materials which create regions of structural weakness and which disadvantageously impact on the mechanical strength of the resulting biomaterial.

The term "gel" encompasses viscous solutions and compositions comprising collagen, which may exhibit flow when in the steady-state. The gel preferably has adhesive or cohesive properties and may be considered as a glue. The viscosity of the gel is preferably controlled in order to ensure optimum infiltration and hydration of the porous collagen-based material at the planned interface. The viscosity of the gel may be between 1-250,000 cP, for example 10, 100, 1000, 10,000, 25,000, 50,000, 100,000, 150,000 or 2000,000 cP. A lower viscosity can result in too much infiltration of the gel into the porous collagen based-material, resulting in an undesirable amount of hydration, which can eliminate the pore structure. A higher gel viscosity can result in insufficient infiltration, which can cause a weak bond between the materials.

The concentration of collagen in the gel may be between 0.1-2% wt/vol. The gel may comprise 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2% wt/vol collagen. The collagen may be Type I collagen, Type II collagen, Type III collagen, Type IV collagen, gelatin, agarose, cell-contracted collagen containing proteoglycans, glycosaminoglycans or glycoproteins, fibronectin, laminin, elastin, fibrin, synthetic polymeric fibres made of poly-acids such as polylactic, polyglycolic or polyamino acids, polycaprolactones, polyamino acids, polypeptide gel, copolymers thereof and/or combinations thereof. The collagen may derive telo-containing collagen, atelo-collagen, or derivatised collagen, or a combination thereof. The term collagen as used herein encompasses recombinant human (rh) collagen. The collagen may be soluble or insoluble and may be derived from any tissue in any animal and may be extracted using any number of conventional techniques.

Step (b) may comprise air drying. Air drying may form weak non-covalent interactions between the porous and non-porous materials that withstand rehydration due to the insolubility of the components of the gel. The temperature and/or humidity of the environment surrounding the biomaterial may be controlled to control the drying rate. Drying a collagen structure in air may cause structural distortions due to the variation in drying rate within the structure, this leading to a physical shape that may not be fit for purpose. In drying step (b) the structure/shape of the materials is preferably substantially retained without distortion. This is important to avoid a decrease in quality of any fabricated biomaterial, which invariably has to precisely fit into defect sites in patients, and where appropriate must have uniform planarity and laminar structure, with minimal or no undesired distortion. The amount of distortion upon drying is influenced by the degree of hydration of the materials when they are joined together. Beyond the deleterious effects of loss of pore structure, excessive hydration should be also avoided—by using only sufficient gel to ensure bonding of the porous and non-porous collagen-based materials—to minimise distortion upon drying. Thus, distortion may be minimised by using only sufficient gel to ensure bonding of the materials.

The importance of controlling the shape/structure of a fabricated biomaterial during the fabrication process has led the applicant to develop methods to ensure that the desired structure, shape, planarity, and laminarity of the biomaterial is retained as it dries. The structure/shape etc. of the biomaterial may be retained by constraining the biomaterial in a cage, mould, press or frame to minimise structural distortion as it dries. Where the biomaterial has a planar or laminar structure the structure/shape may be retained by sandwiching the biomaterial between rigid sheets as it dries. The structure/shape may be retained by adhering or attaching a surface other than the bonding surface of the non-porous material to a substrate. The cage, mould, press, frame, rigid sheets, and/or substrate is preferably metallic or manufactured from a material sufficiently rigid to constrain/prevent distortion of the drying biomaterial. The cage, mould, press, frame, rigid sheets, and/or substrate may comprise or be coated with a non-stick material, for example polytetrafluoroethylene.

Collagens are provided by each of the porous and non-porous collagen-based materials, as well as in the bonding layer of gel comprising collagen. The cross-linking step is preferably employed to cross-link or bioconjugate the collagens in the bonding layer with those provided by the porous and non-porous collagen-based materials. Because the collagen applied at the interface between the materials partially hydrates an inwardly extending section of the porous collagen based-material, the cross-linking further joins the collagen based-material and the non-porous collagen based-materials by providing covalent cross-inking to the interfacial structure. The cross-linking step may also cross-link collagens in the porous collagen based-material, and in the non-porous collagen based-material. Cross-linking provides added stability and renders the collagen molecules resistant to collagenase and other matrix metalloprotease activity in vivo. The cross-linking step may comprise the use of one or more suitable chemical or biological agents or physical cross-linking methodologies with the proviso that the cross-linking does not require that the biomaterial is washed to remove potentially cytotoxic end- or by-products, such as aldehydes, a step which risks fully hydrating the biomaterial and causing undesirable loss of pore structure and/or distortion of structure/ shape upon drying. The cross-linking may be a combination of physical and/or chemical/biological methodologies.

The gel preferably comprises components which can facilitate the cross-linking of the collagens in the bonding layer. The gel may further comprise a glycosaminoglycan (GAG) or mucopolysaccharide. Glycosaminoglycans are a family of macromolecules containing long unbranched polysaccharides containing a repeating disaccharide unit. Preferably, the glycosaminoglycan is selected from one or more of chondroitin sulphate, dermatin sulphate, heparin, heparin sulphate, keratin sulphate and hyaluronic acid. Chondroitin sulphate may be chondroitin-4-sulphate or chondroitin-6-sulphate, both of which are commercially available, for example, from Sigma-Aldrich Inc. The chondroitin-6-sulphate may be derived from shark. The GAG may be used at 0.01 to 12 (dry) wt %, or 1 to 5.5 (dry) wt %, or 1.8 to 2.3 (dry) wt %. Preferably the GAG is used at 0.1% wt/vol. The gel may comprise other polysaccharides or other components which can provide cross-linking functionality. The composition of the gel may be the same as the composition of the porous and/or non-porous collagen-based material. The concentration of the collagen and GAG in the gel may be the same as the concentration of the collagen and any GAG in the porous collagen-based material.

Various physical cross-linking methodologies may be used to cross-link the collagens in the bonding layer. The cross-linking step may comprise a dehydrothermal (DHT) treatment applied to the dried biomaterial to provide a condensation reaction which bonds amine and carboxylic acid groups. The advantage of DHT treatment is that no chemical reagent is required and no potentially cytotoxic end or by-products are created during the treatment. The biomaterial may be heated in a vacuum. The temperature and exposure period of the DHT treatment may be varied to alter the compressive and tensile properties and cross-linking density of the biomaterial. The temperature of the DHT treatment may be between 60-180 degrees Celsius, with an exposure between 24-120 hours. The vacuum may be e.g. 50-150 mTorr.

The cross-linking may be photo-induced. The cross-linking step may comprise UV or visible light treatment. UV irradiation (at 254 nm) is a rapid and easily controlled means of increasing the mechanical strength of collagen fibres and does not produce any toxic by-products which require subsequent removal by washing the biomaterial. The collagen gel may comprise hydroxyl containing components such as polysaccharides or GAGs, which may optimise the UV cross-linking treatment. The collagens may be cross-linked using visible light in the presence of photosensitiser dyes such as methylene blue and rosebengal.

The cross-linking step may comprise DHT treatment and UV treatment, or a combination of cross-linking methodologies.

The cross-linking step may comprise radiation treatment, using electron beam (EB) or gamma rays. Consistent with the majority of the physical cross-linking methodologies, radiation-induced cross-linking does not require the use of cytotoxic cross-linkers and no subsequent treatment steps are necessary. Another advantage of radiation-induced cross-linking is that gamma rays can penetrate the biomaterial to depths that may not be achieved using other methodologies such as visible light or UV light-induced cross-linking.

Whilst physical cross-linking methodologies advantageously do not result in the formation of cytotoxic end- or by-products, one or more chemical cross-linking agents, preferably used in the vapour phase, can be employed to cross-link the collagens in the bonding layer. Chemical cross-linking reagents are molecules that contain two or more reactive ends capable or chemically attaching to specific functional groups (primary amines, sulfhydryls, etc.) on proteins. Preferably, the chemical cross-linking agent should not result in the formation of non-volatile side products. The vapour phase chemical cross-linking agents may be selected from the group consisting of: glutaraldehyde, formaldehyde, and hexamethyldiisocyanate. The cross-linking agent may be selected from the group consisting of: carbodiimides, polyaldehydes, polysulfones, activated PEGs, epoxides, imidazoles and diisocyanates. The cross-linking step may comprise treatment with an aldehyde such as glutaraldehyde or formaldehyde (which can cross-link lysine residues), 1-ethyl-3-(3-dimethyl amino propyl) carbodiimide hydrochloride (EDC) (which can cross-link amino and carboxyl groups), or polyepoxy compounds such as glycerolpoly(glycidylether) and poly(ethyleneglycoldiglycidylether). The cross-linking agent may be hexamethylene diisocyanate (HMDI), which can cross-link amino groups. EDC is a preferred cross-linking agent because it does not become part of the final cross-link between collagen molecules.

The gel may further comprise components (e.g. GAGs) that are modified or derivatised to comprise reactive groups that react with the non-porous and porous collagen materials to achieve cross-linking without the release of potentially cytotoxic by- or end-products. The components may be chemically functionalised with aldehyde reactive groups or NHS activated ester groups. The components may be triazine activated collagen or epoxide functionalised collagen.

The gel may be acidic or alkaline prior to being applied to the bonding surface. The gel may gelate at neutral pH. The pH of the gel may be neutralised upon application to the bonding surface. The gelation time of the gel may be 1-60 minutes after neutralisation. Cross-linking may occur as the pH of the gel neutralises after application, causing fibrillogenesis in the gel, i.e. the development of fine fibrils normally present in collagen fibres of connective tissue.

As collagen contains both nucleophilic and electrophilic groups it is can self-cross-link using many of the chemistries described above. In a preferred embodiment a gel is used in which intergel cross-linking reactions are prevented or minimised thereby allowing a cross-linking gel to be applied without premature strengthening of the gel. The gel may comprise collagen in combination with polyethylene glycol and/or glycosaminoglycans.

In the fabrication process one or more pieces or regions of non-porous collagen-based material may be joined to one or more pieces or regions of porous collagen-based material. As will be described below the process can be used to fabricate novel biomaterial formats which comprise multiple regions of porous and non-porous collagen-based material. The formats may mimic the composition and/or structure of tissues including bone, cartilage, tendon, ligament and the interfaces between these tissues.

According to a second aspect of the present invention there is provided a fabricated biomaterial comprising porous and non-porous collagen-based materials bonded with a bonding layer of dried gel comprising collagen. The biomaterial may be multi-phase and may be continuous. The fabricated biomaterial of the invention is defined as multiphase because it comprises both porous and non-porous collagen-based materials, i.e. one or more phases having a required porosity and one or more phases having required mechanical strength.

The invention may also utilise a novel cross linking sequence in order to achieve the construction of a multiphase biomaterial which comprises both non-porous and porous collagen-based materials.

The porous and non-porous collagen-based materials may further comprise other biopolymeric components such as glycosaminoglycans (e.g. chondroitin 4-sulfate, chondroitin 6-sulfate, keratan sulfate, dermatan sulfate, heparan sulfate, hyaluronic acid or chitosan), proteoglycans (e.g. decorin), proteins (e.g. elastin, resilin or other components of the extracellular matrix).

One or both of the porous and non-porous collagen-based materials may be cross-linked prior to being joined together. Cross-linking of the separate components provides mechanical strength which can improve the physical and mechanical properties of a biomaterial fabricated by the process of the invention. Preferably, at least the porous collagen-based material is cross-linked prior to being employed in the fabrication process. This ensures that the material does not weaken, break-up or disintegrate upon rehydration by the bonding layer of gel.

The porous collagen-based material may be unmineralised or mineralised. In embodiments where one or more phases, pieces, or regions are required to mimic bone, the porous collagen-based material may be mineralised and may comprise a calcium phosphate, for example brushite, octacalcium phosphate, apatite hydroxyapatite, $\beta$-tricalcium phosphate, biphasic calcium phosphate, substituted calcium phosphate, silicate-substituted calcium phosphate, silicate-substituted hydroxyapatite, or silicate-substituted tricalcium phosphate. The porous collagen-based material may comprise a co-precipitate of collagen and glycosaminoglycan or calcium phosphate, or a triple co-precipitate of collagen, glycosaminoglycan and a calcium phosphate material. The collagen and the one or more glycosaminoglycans may be cross-linked.

The percentage of open-cell porosity (measured as a percentage of the total number of pores both open- and closed-cell) in the porous material is preferably from 1 to 100%, more preferably from 20 to 100%, and still more preferably from 90 to 100%.

The collagen is preferably present in the material in an amount of from 5 to 90 (dry) wt %, more preferably from 15 to 60 (dry) wt %, more preferably from 20 to 40 (dry) wt %.

The one or more glycosaminoglycans may be present in the material in an amount of from 0.01 to 12 (dry) wt %, more preferably from 1 to 5.5 (dry) wt %, most preferably from 1.8 to 2.3 (dry) wt %. Preferably, the ratio of collagen to the total amount of one or more glycosaminoglycans is from 8:1 to 30:1 by weight (dry), more preferably from 10:1 to 30:1 by weight (dry), still more preferably 10:1 to 12:1 by weight (dry), and most preferably 11:1 to 23:2 by weight (dry).

The bonding layer may be between 50-100 µm (microns) in thickness.

The collagens in the bonding layer may be cross-linked. The collagen in the porous and/or non-porous collagen-based materials may be cross-linked. The biomaterial may be cross-linked to provide multiple different mechanical and/or degradation characteristics. The collagen and the glycosaminoglycan in the porous or non-porous collagen-based materials may be cross-linked.

Due to the controlled amount of hydration of the porous collagen-based material in the fabrication process, the biomaterial advantageously retains >95% of the original porosity of the porous collagen-based material.

The non-porous collagen-based material may comprise an extruded collagen sheet or membrane, or collagen fibres (e.g. in a bundle), which may be extruded and/or aligned. Extruded collagen structures, including fibres (both woven and non-woven) and sheets, reconstituted from insoluble and soluble collagen are well known to those skilled in the art, as are porous materials based on collagen and a range of combined biopolymeric materials. However, their usage in combination has been limited due to that inability to successfully integrate these materials into single structures. The non-porous collagen may also be a purified animal or human derived tissue, such as decellularised skin, intestine, periosteum, pericardium, fascia or other xenograft or allograft sheets that are well known to those skilled in the art.

The biomaterial may be an unmineralised porous patch comprising a non-porous collagen membrane bonded to a porous collagen-based material comprising collagen and a GAG. The unmineralised porous patch may comprise more than one region of the porous collagen-based material, and it is envisaged that patches of various shapes/sizes can be fabricated using the method of the present invention. The non-porous collagen-based material may overlap the porous collagen-based material to provide a flap to enable fixation of the device in a defect site of a patient. The fixation may be achieved by using techniques known to those skilled in the art such as suturing, tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids.

The non-porous collagen-based material may act as a barrier to the transport of cells, proteins, and small molecules out of the porous collagen-based material.

The porous collagen-based material may comprise a porous collagen scaffold and the non-porous collagen-based material may comprise aligned collagen fibres. The biomaterial may comprise multiple regions of porous and/or nonporous collagen-based materials. The biomaterial may comprise non-porous aligned collagen fibres having a porous mineralised collagen-based material at each end.

There is provided a fabricated biomaterial produced by the process according to the first aspect of the invention.

According to a further aspect of the present invention, there is provided an implant comprising the fabricated biomaterial of the invention. The implant may comprise one or more phases, pieces or regions of porous and/or non-porous collagen-based material.

According to a further aspect of the present invention, there is provided a synthetic cartilage, bone, ligament, tendon, meniscus, periodontal tissue, dentine, enamel, intervertebral disc, annulus fibrosus, or nucleus pulposus implant, graft, substitute, scaffold, filler, coating or cement comprising a biomaterial or implant according to the present invention.

The biomaterial or implants comprising the biomaterial of the invention may further comprise cells. The cells may be stem or progenitor cells, differentiated cells, terminally differentiated cells, or combinations thereof. The cells may be totipotent, pluripotent or unipotent stem cells, or induced pluripotent stem cells. The cells may be human embryonic stem cells, derived via a technology which does not necessitate the destruction of the human embryo, for example via an established cell line. Mesenchymal stem cells (also referred to as marrow stromal cells, multipotent stromal cells, or MSCs) are pluripotent stem cells which can differentiate into a variety of cell types including osteoblasts, tenocytes, chondrocytes, myocytes, adipocytes. These cell types have the ability to generate bone, tendon, ligament, cartilage, muscle, and fat. The cells may be MSCs or any cell within the MSC lineage. Progenitor cells can go through several rounds of cell division before terminally differentiating into a mature cells, and the cells may be these intermediary cells. The cells may be selected from the group consisting of: MSCs (marrow stromal cells, mesenchymal stem cells, multipotent stromal cells), chondrocytes, fibrochondrocytes, osteocytes, osteoblasts, osteoclasts, synoviocytes, adipocytes, bone marrow cells, mesenchymal cells, stromal cells, genetically transformed cells, or combinations thereof. The cells may be autologous or heterologous.

The cells may include one or more of the following: embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells.

Using the above-described fabrication process it is possible to combine collagen sheets, fibres with mineralised and non-mineralised porous components thus enabling the fabrication of a number of different configurations and formats that mimic the structure of human tissues. Some of the applications of the biomaterials produced using the recited fabrication process are detailed below.

In one embodiment the biomaterial may simulate a bone-tendon insertion structure known as Sharpey's Fibres, essentially a matrix of connective tissue comprising bundles of strong collagenous fibres connecting periosteum to bone. The biomaterial comprising substantially parallel non-porous collagen fibres (parallel along the long axis of the implant) and further comprising a porous mineralised collagen-based material at one or both ends (i.e. one or two regions of porous collagen-based material comprising collagen, a GAG and calcium phosphate). The biomaterial may comprise loops suitable for suturing at each end.

In another embodiment, the biomaterial may be used to fill a defect in the meniscus. The meniscal implant can be designed to fit into the defect site and fixed in place by standard techniques such as suturing, tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids. The suturing may be done through the porous part of the device and/or the non-porous part as appropriate, in order to fix the device in place.

In a further embodiment, the biomaterial may be used as an arterial closure device. The device can be designed such that the porous part fits into the artery and the non-porous part folds over and around the artery in a manner to provide closure. The device can then be fixed in place by any standard techniques such as suturing, tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids. The suturing may be done through the porous part of the device and/or the non-porous part as appropriate, in order to fix the device in place.

Patches for the regeneration of articular cartilage can be fabricated, these utilising the porous material to deliver cells or (macro)molecular species whereas the non-porous material enables fixation to surrounding tissues and prevents loss of components loaded into the porous material. The patches can be fabricated based on a combination of a porous collagen sheet with a collagen based fibre construct, such as a fabric, which provides suturability. Alternatively, a combination of a porous collagen sheet, such as an extruded collagen sheet, can be combined with a non-porous collagen sheet, which provides suturability and impermeability. In one embodiment an implant is provided which comprises an unmineralised porous patch, i.e. a porous collagen-based material comprising collagen and a GAG bonded to a non-porous collagen sheet. This structure is of particular utility as a scaffold for enhancement of a chondral stimulation technique known as microfracture, where puncturing sub chondral bone is utilised to generate fibrocartilage to cover chondral defects. In addition, this material structure is particularly useful in the application of autologous chondrocytes implantation procedures, where chondrocytes are implanted into chondral defects in articular cartilage. A specific advantage of this material, if utilised for a matrix-assisted autologous chondrocytes implantation procedure is that the porous layer can deliver a cell-loaded porous material that closely conforms to the defect shape.

Biomaterials and implants for regeneration of tendons and ligaments can be fabricated, using (i) a mineralised and non-mineralised material combination which mimics the bone-tendon interface, or (ii) a porous collagen sheet combined with a non-porous bundle of collagen fibres to provide a material that can be used to augment tendon regeneration. Patches for the repair of bone-ligament/tendon interfaces can be fabricated using porous mineralised calcium phosphate collagen blocks combined with a non-porous bundle of collagen fibres.

The fabrication process of the invention may comprise fabricating the formats described herein, by joining non-porous collagen-based material to porous collagen-based material, as described previously.

There is provided a use of a collagen gel to bond porous and non-porous collagen-based materials.

According to a further aspect of the present invention there is provided a method of treatment of a defect in a target tissue of a patient comprising: taking a biomaterial or implant according to the present invention and inserting the material into the defect of the patient.

According to a further aspect of the present invention there is provided a method of organ or tissue engineering in a patient, comprising the step of replacing a target tissue in the patient with a biomaterial or implant according to the present invention.

According to a further aspect of the present invention there is provided a use of a biomaterial or implant according to the present invention to treat a defect in a target tissue of a patient. There is provided a use of a biomaterial or implant according to the present invention in the manufacture of a medicament to treat a defect in a target tissue of a patient.

There is provided a use of a biomaterial or implant according to the present invention in tissue engineering of a target tissue of a patient. There is provided a use of a biomaterial or implant according to the present invention in the manufacture of a medicament to tissue engineer a target tissue of a patient.

The target tissue may be selected from the group consisting of: cartilage, bone, ligament, tendon, artery, Sharpey's fibres, meniscus, periodontal tissue, dentine, enamel, intervertebral discs, annulus fibrosus, and nucleus pulposus.

The patient may be a mammal, or a non-human mammal. The patient may be a human, dog, camel, or horse.

According to a further aspect of the present invention there is provided a kit of parts comprising a biomaterial or implant according to the present invention, in combination with a delivery device. The kit may comprise a plurality of biomaterials, implants, delivery devices, or combinations thereof. The kit may further comprise additional tools which may be required in procedure utilised to deliver the implant, or engineer the tissue or organ.

Figure 2:
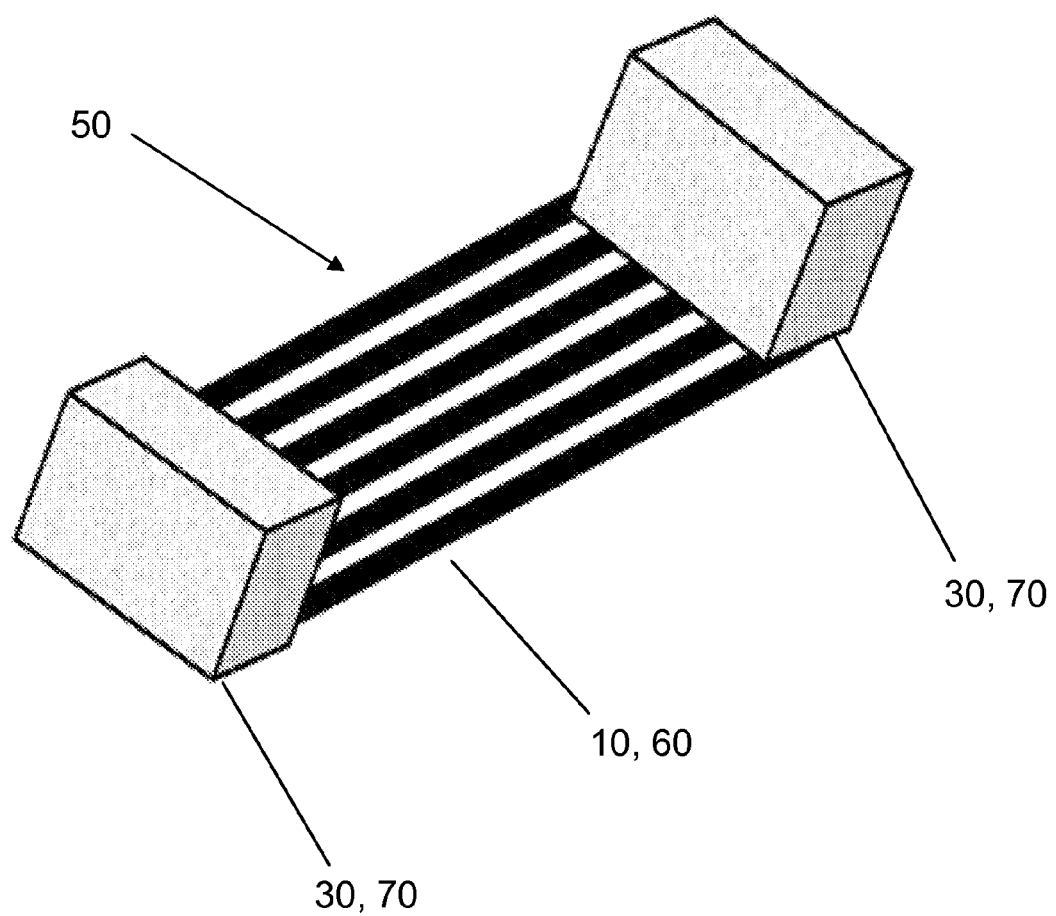
Figure 3A:
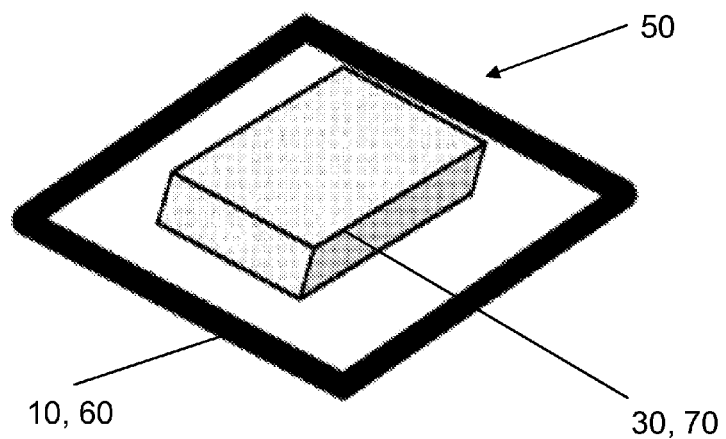
Figure 3B:
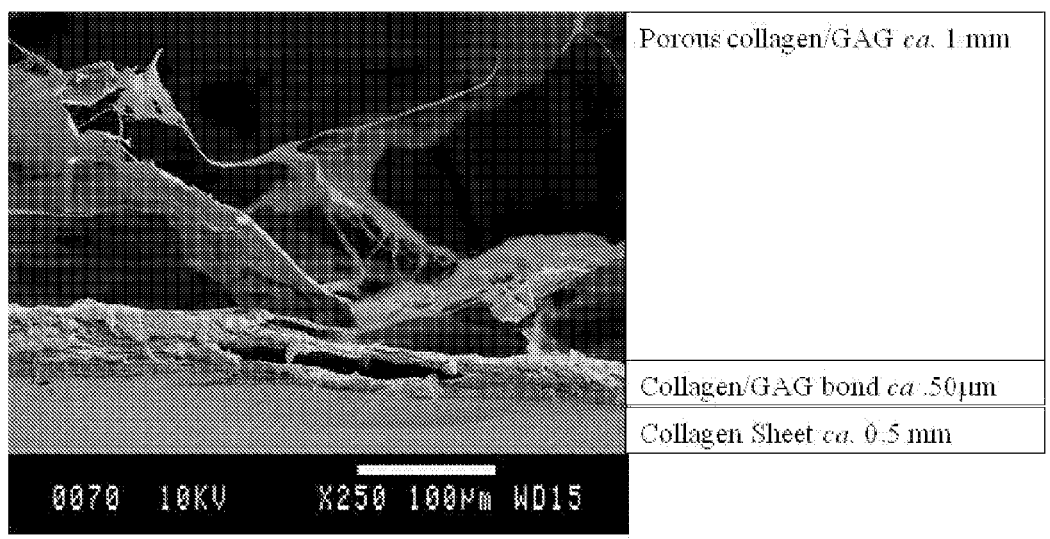
Figure 4A:
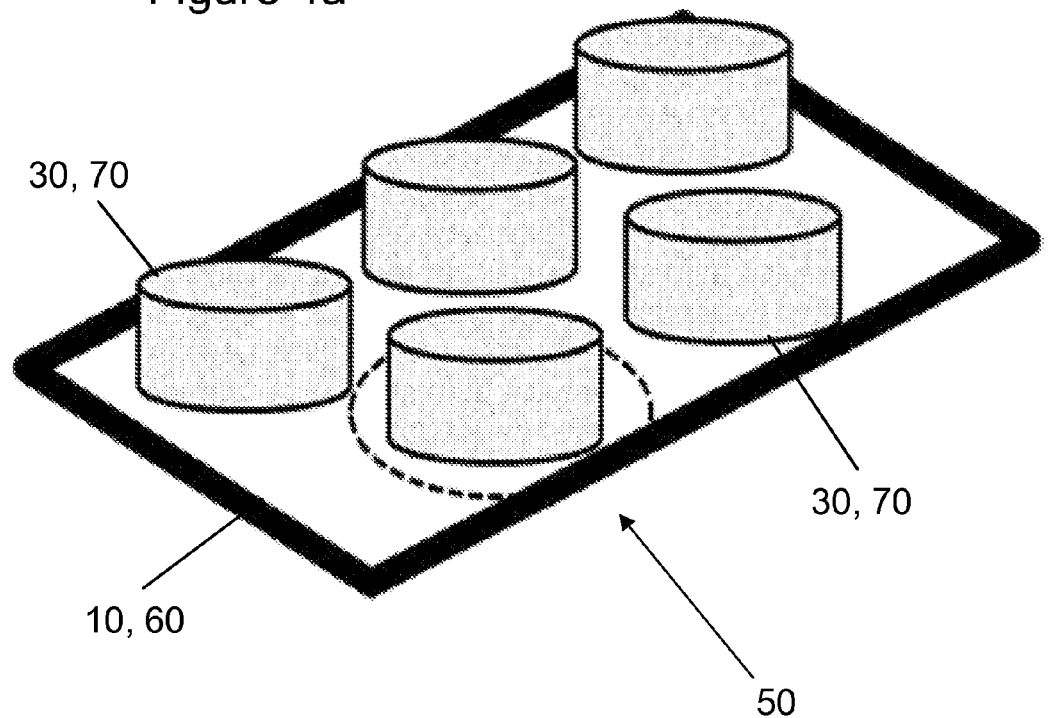
Figure 4B:
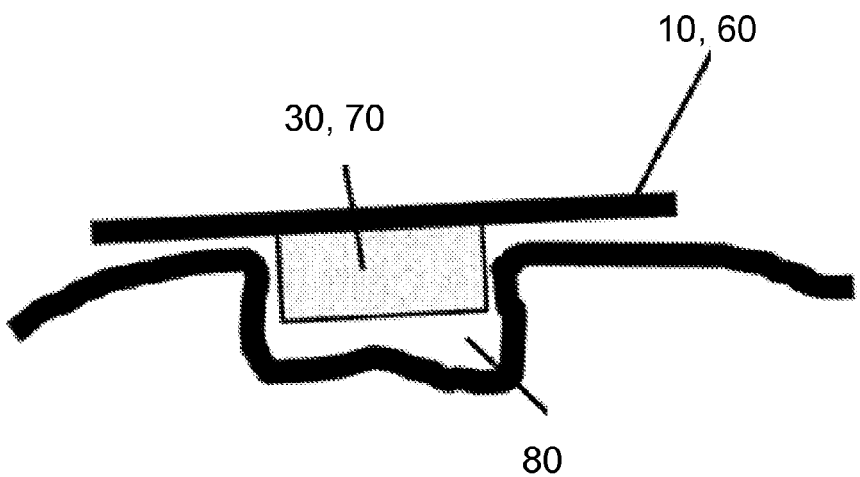
Figure 5B:
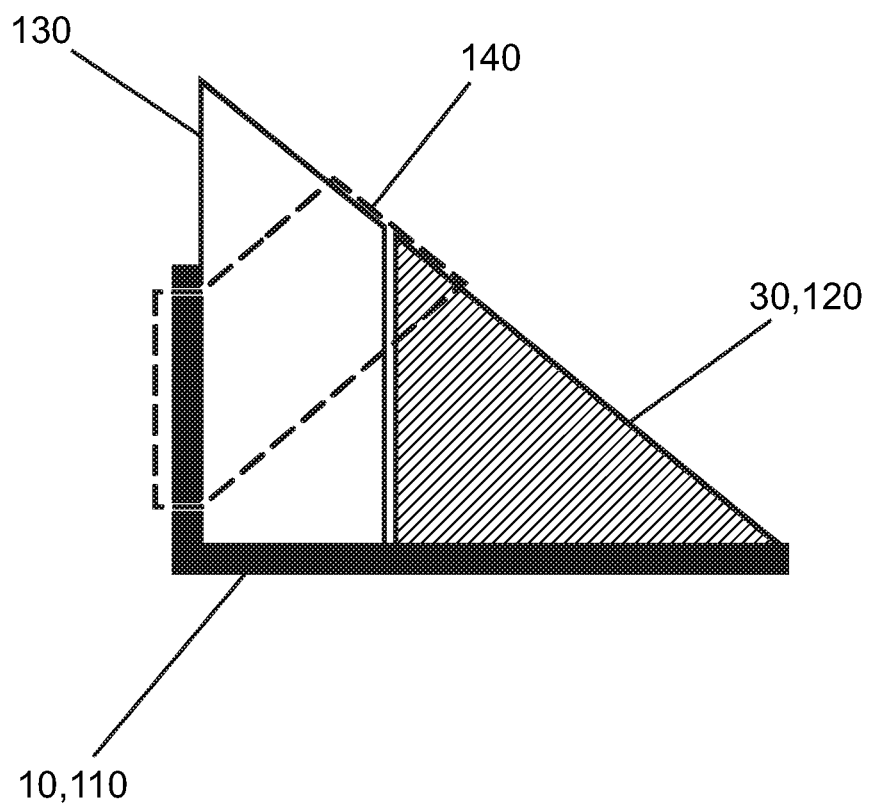
Figure 6A:
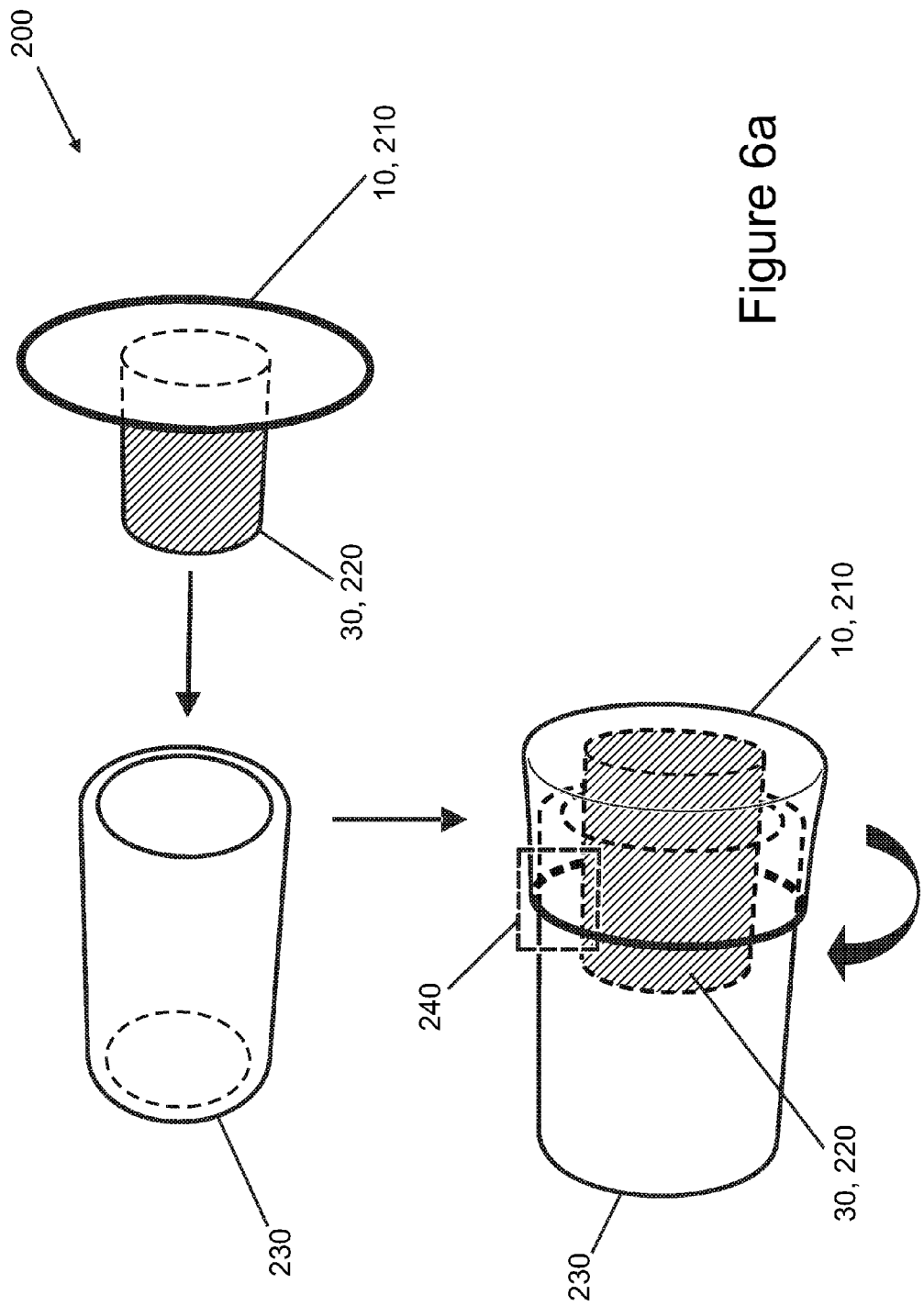
Figure 6B:
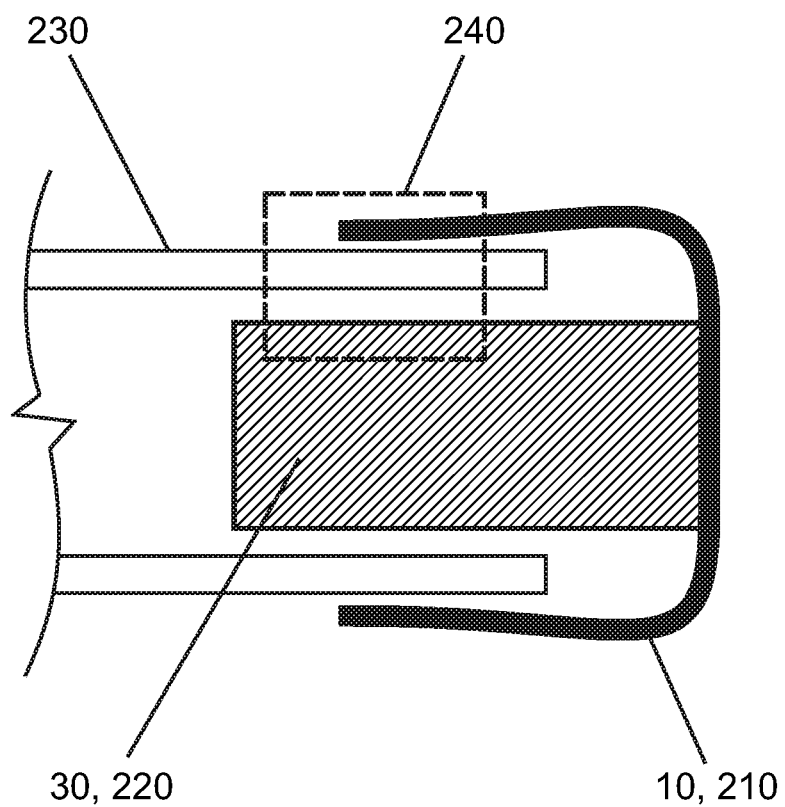

The present invention will now be described further by way of example and with reference to the following drawings in which:

FIG. 1: shows a schematic detailing the process for the controlled gel bonding of porous and non-porous collagen-based materials components;

FIG. 2: shows the configuration of a three-region multiphase implant suitable for the regeneration of fibrous connective tissue with bone;

FIG. 3a: shows a two-layer tissue repair membrane;

FIG. 3b: shows the structure of a two-layer tissue repair membrane under scanning electron microscope;

FIG. 4a: shows an assembly of multiple different shapes and sizes of porous collagen on an extruded collagen sheet;

FIG. 4b depicts the use of the product in treatment of a defect in a tissue;

FIG. 5a: shows a schematic for placing an implant at a defective site on the meniscus;

FIG. 5b: shows a cross-section of the meniscal implant fixed in position by sutures;

FIG. 6a: shows a schematic for use of the product as an arterial closure device, and FIG. 6b: shows a cross-section of the arterial closure device fixed in position by sutures.

MATERIALS

Collagen: Type I, microfibrillar collagen from bovine tendon, Integra Life Sciences Plainsboro, N.J., USA GAG: Chondroitin-β-sulphate from shark cartilage, sodium salt, Sigma-Aldrich Inc (St. Louis, Mo., USA) Calcium Sources: (i) Calcium hydroxide (Ca(OH)2), Sigma-Aldrich Inc (St. Louis, Mo., USA); (ii) Calcium nitrate (Ca (NO3) 2.4H2O), Sigma-Aldrich Inc (St. Louis, Mo., USA) Phosphorous Source: Orthophosphoric acid (H3PO4), BDH Laboratory Supplies (Poole, United Kingdom) Cross-linking Agents: 1-Ethyl-3-(3-Dimethylaminopropyl) Carbodiimide (=EDAC), Sigma-Aldrich Inc (St. Louis, Mo., USA); N-Hydroxysuccinimide (=NHS), Sigma-Aldrich Inc (St. Louis, Mo., USA).

Referring to FIG. 1, the schematic shows the preferred method of fabrication which comprises a sequence of steps which can be applied in whole or in part, to produce the fabricated biomaterials of the invention. The initial steps involve hydrating a non-porous collagen-based material (10), most preferably an extruded sheet or membrane, or a bundle of fibres, with a bonding layer of a collagen-based gel. The non-porous material (10) is dosed with a specific amount of the gel, typically 50-500 µL cm$^{-2}$ to ensure that the resulting bond is of an appropriate thickness for bonding the materials together, and which is not so excessive as to damage the porosity or create distortion problems upon subsequent drying. The inventors have experimentally determined that an appropriate thickness of the bonding layer is 50-100 µm. In step (iii) the hydrated non-porous material (20) is then joined to the porous collagen-based material (30) by gently pressing the porous collagen-based material (30) onto the hydrated non-porous material (20) so as to contact the bonding layer of gel (40). The capillary forces at the interface between the materials (20, 30) draw a limited amount of the gel into the porous collagen-based material (30) resulting in partial hydration of a narrow section of the porous collagen-based material (30) at the interface between the two materials. Preferably, the porous collagen-based material is cross-linked to provide mechanical strength, and which minimises the tendency of the material to weaken or disintegrate upon contact with the bonding layer of gel. Although not shown, multiple regions or pieces of porous collagen-based material can be joined to one or more regions or pieces of non-porous collagen-based material. Step (iv) comprises drying the joined materials with minimal distortion to the physical structure (shape, size) to bond them together, to form a fabricated continuous, multiphase biomaterial (50). Although not shown, the structure, shape, planarity, laminarity of the biomaterial is retained by minimising and ideally preventing distortion upon drying. This can be achieved by physically constraining the biomaterial, for example in a cage, mould or frame, or by inserting it between rigid sheets, or by adhering the non-porous collagen-based material to a rigid non-distortable substrate. Preferably step (iv) comprises cross-linking the collagens and any other cross-linkable components in the gel to provide a stronger bond. Biomaterial (50) is defined as "continuous" because the two materials (10, 30) are bonded and cross-linked together, and "multiphase" because the biomaterial comprises porous and non-porous regions having different functionalities and properties.

Referring to FIG. 2, the configuration of an implant suitable for the regeneration of fibrous connective tissue with bone is shown. The implant consists of fabricated biomaterial (50) comprising non-porous region (60) and two porous regions (70). Non-porous region (60) comprises non-porous collagen-based material (10) in the form of extruded collagen. Porous regions (70) comprise porous mineralised collagen-based material (30) comprising collagen, a glycosaminoglycan and calcium phosphate. The porous regions (70) are essentially blocks of mineralised collagen/GAG which mimic the structure of bone. The blocks can be attached to each end of the extruded collagen using a bonding layer of adhesive collagen gel (not shown). The collagens in the bonding layer of gel can be cross-linked to the collagens in the non-porous and porous collagen-based materials, for example via DHT treatment. The implant can be anchored in bone at each end, and can be used to repair, replace or augment ligaments and tendons. The implant depicted in FIG. 2 was fabricated as described below.

An extruded collagen fibre was produced according to methods previously described, for example in U.S. Pat. No. 5,171,273. Insoluble or soluble collagen, extruded into an aqueous solution (pH ~7.5, at 37° C.) produced a collagen fibre with sufficient mechanical strength to be processed. The extruded collagen fibre was spooled to provide a fibre structure which contains substantially parallel fibres along the long axis and contains loops at the terminal ends, which provide suturable attachment points. The collagen fibre loop was then cross-linked via immersion in a cross-linking solution comprising N-hydroxysuccinimide (NHS) and 1-ethyl-3-(3-dimethyllaminopropyl)carbodiimide (EDC) in MES buffer (pH 5.5) for one hour before being washed with deionised water and air dried. The collagen fibre bundle was cast in a collagen-chondroitin-6-sulphate gel prepared via blending an acidified gel comprising 1 g freeze dried collagen, 0.1 g chondroitin-6-sulfate and 100 mL 20 mM HCl. The amount of gel used was 50 µL per cm$^2$. The collagen-GAG gel was allowed to hydrate the fibre bundle and fill the interstitial apace between the fibres. No excess collagen/GAG gel was present.

The porous collagen-glycosaminoglycan-calcium phosphate material was prepared according to methods previously developed by the applicant (disclosed in WO 2005/051447, WO 2006/095154 and WO 2008/017858). The process described in WO 2005/051447 involves: providing an acidic aqueous solution comprising collagen, a calcium source and a phosphorous source and a glycosaminoglycan; and precipitating the collagen, the brushite and the glycosaminoglycan together from the aqueous solution to form a triple co-precipitate. Beyond the use of the applicant's triple co-precipitated porous collagen-based material, it is envisaged that other porous collagen-based materials can be used in the fabrication method of the invention to produce continuous fabricated multiphase biomaterials and implants having desired porosity and strength. After preparation, the porous material was cut using a scalpel or similar device to form bone blocks of the dimensions approximately 10×10×12 mm.

Before the collagen/chondroitin-sulfate gel was allowed to dry, the porous collagen-glycosaminoglycan-calcium phosphate blocks were placed to the gel in the configuration shown (see FIG. 2). As described above, the process involved the partial wetting of the porous material with the collagen/chondroitin-6-sulfate gel such that the pores were partially filled in a thin layer at the interface thus allowing a mechanically strong bond to be made between the porous material and the non-porous material. The biomaterial was then allowed to air dry with minimal distortion of the structure. Cross-linking— via the application of a dehydrothermal treatment of 105° C. at 150 mTorr for three days—was used to further enhance the mechanical strength of the collagen-GAG bond in the implant. The resulting implant resembles a bone-patellar-bone or anterior cruciate ligament configuration.

The fabrication process can be used to generate biomaterials comprising porous blocks bonded to a non-porous extruded collagen sheet, as shown in FIG. 3. The depicted biomaterial (50) comprises non-porous region (60) and porous region (70). Non-porous region (60) comprises an extruded collagen sheet (10) and porous region (70) comprises collagen and a glycosaminoglycan (30). The crosslinked porous region (70) is bonded to the extruded collagen sheet (10, 60) using a bonding layer of adhesive collagen gel (not shown). This material was fabricated as detailed below.

An extruded collagen film was used as the substrate for the attachment of a porous collagen sheet to enable the assembly of a scaffold comprising both an impermeable collagen sheet and a porous collagen/GAG sheet. The collagen sheet was extruded as per any of a number of industrial processes for the production of collagen sheet having a thickness of approximately 0.5 mm. The fabrication procedure initially involved the hydration of the collagen sheet with 50 μL per cm$^2$ of 1% w/v collagen gel. The hydrated sheet was laid flat on a Teflon (RTM) substrate to minimise distortion and maintain planarity. A porous crosslinked collagen/GAG layer was then laid onto the extruded collagen sheet and the gel was allowed to partially hydrate the surface of the porous collagen/GAG layer. The assembled biomaterial was then allowed to air dry with minimal distortion to the physical shape and dimensions of the components. The resulting bonded biomaterial comprised a substantially impermeable collagen sheet, a collagen/GAG bonding layer of approximately 50 microns in thickness and a porous collagen/GAG scaffold of approximately 1 mm in thickness, as shown in FIG. 3b. This material can subsequently be cross-linked using physical or chemical cross-linking methodologies, as described previously. The bonding together of a porous collagen-based material with an extruded collagen sheet creates a biomaterial having a substantially impermeable layer which enables the porous layer to be loaded with species such as cells, proteins or other macromolecular components without their leakage into the surrounding environment after delivery. The extruded collagen sheet is of sufficient mechanical strength to support tensile loads of greater than 5 N. This mechanical strength enables the sheet to be attached to soft tissue via a variety of orthopaedic fixation techniques including, but not limited to, suturing, tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids.

Combining porous and non-porous collagen-based materials using the process of the invention also enables the production of a biomaterial which can be used as a stabilised plug, whereby an overlap of the non-porous material provides structural stabilisation of the porous material when it is inserted into a defect site. Examples of the defect site for which this format is most applicable includes (i) cartilage defects, (ii) tooth extraction sockets, (iii) skin injury and (iv) meniscal defect.

FIG. 4a depicts a sheet of biomaterial (50) comprising multiple different shapes and sizes of porous collagen (30, 70) on an extruded collagen sheet (10, 60) such that the individual components can be selected via cutting out individual pieces or can be used as an assembly to provide porous scaffold into multiple proximate sites. The porous regions (70) are bonded to the extruded collagen sheet using a bonding layer of adhesive collagen gel (not shown). A schematic detailing how this biomaterial may be applied into a soft tissue defect site (80) is shown in FIG. 4b.

FIG. 5a show a schematic detailing a meniscal defect filling device (100) according to the present invention for inserting into a defect in the meniscus (130). The defect site is a resected meniscus with an intact outer meniscal rim. The porous section (120) of the device (100) is formed so as to fit into the defect site of the meniscus (130) and is attached to the non-porous part (110) which folds around the meniscus (130). The implant (100) can be fixed into place by fixing means such as sutures (140). Other fixing means may also be used such as tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids or any other means known to the person skilled in the art. FIG. 5b shows a cross-section at the meniscus (3)) with the implant (100) fixed in place by sutures (140) at the defect site.

A further application of the present invention may be as an arterial closure device as illustrated in the FIG. 6a schematic. The arterial closure device (200) is formed of a non-porous part (210) and a porous part (220) according to the present invention. The porous part (220) is designed to fit into the artery (230) and the non-porous part (210) is designed to be flexible enough to wrap around the external surface of the arterial wall in order to provide closure. Once the device (200) is in place, it can be fixed to the artery (230) by sutures (240). Other appropriate fixing means may also be used such as tacking, use of darts, use of composite devices such as devices comprising sutures and polymeric tabs or buttons, suture passing devices, bioadhesives such as fibrin glues, techniques involving the induction of fibrin clots or techniques based on the formation of adhesives from other autologous body fluids. FIG. 6b shows a cross-section of the arterial closure device (200) in situ.

In summary the applicant has developed a fabrication process capable of producing novel formats of biomaterials advantageously having both porosity and mechanical strength. The process relies on the use of a bonding layer of gel comprising collagen to join non-porous and porous collagen-based materials. The hydration of the materials used in the process and the drying of the resulting biomaterial are tightly controlled to maintain the required porosity and the structure/shape of the biomaterial. Physical confinement may be used in the drying to impose three dimensional structure to the biomaterial without distortion of the porous component during the drying process. The process preferably comprises a cross-linking step which does not result in the production of potentially cytotoxic end- or by-products (which ordinarily require removal via subsequent washing steps). The chemistry of the gel may be catered to the type of cross-linking employed. This process is substantially superior to other methods of construction, such as freeze drying fully dense materials, casting in a collagen gel or mechanical integration where much of the structure and properties of the individual components are lost. In particular, the invention enables the integration of an aligned dense non-porous collagen material, such as a fibre or aligned sheet, with a porous material, thus mimicking the structure of the bone-tendon or bone-ligament interface.

The invention claimed is:

1. A process for fabricating a biomaterial, comprising
   a) joining a porous collagen based-material with a non-porous collagen based-material by applying a controlled amount of a bonding layer of a gel comprising collagen to a bonding surface of the non-porous collagen based-material, and contacting a surface of the porous collagen based-material with the gel applied to the bonding surface to partially hydrate a section of the porous material at the interface between the materials;
   b) drying the gel to bond the materials together; and
   c) cross-linking the collagens in the bonding layer.

2. The process of claim 1 wherein in drying step (b) the structure/shape of the materials is substantially retained without distortion.

3. The process as claimed in claim 1 wherein step (b) comprises air drying.

4. The process as claimed in claim 1 characterised in that the gel is acidic or alkaline prior to being applied to the bonding surface.

5. The process as claimed in claim 4 wherein gelation of the gel takes place at neutral pH.

6. The process as claimed in claim 1 wherein the gel further comprises a glycosaminoglycan selected from the group consisting of: chondroitin 4-sulfate, chondroitin 6-sulfate, keratin sulfate, dermatan sulfate, heparin sulfate, and hyaluronic acid.

7. A fabricated biomaterial comprising porous and non-porous collagen-based materials bonded with a bonding layer of dried gel comprising collagen, wherein the collagens in the bonding layer are cross-linked.

8. The biomaterial as claimed in claim 7 wherein the bonding layer is 50-100 micrometers in thickness.

9. The biomaterial as claimed in claim 7 wherein the collagen in the porous and/or non-porous collagen-based materials is cross-linked.

10. The biomaterial as claimed in claim 7 wherein the porous collagen-based material comprises a calcium phosphate.

11. The biomaterial as claimed in claim 10 wherein the calcium phosphate is selected from the group consisting of: brushite, octacalcium phosphate, apatite, hydroxyapatite, β-tricalcium phosphate, biphasic calcium phosphate, silicate-substituted calcium phosphate, silicate-substituted hydroxyapatite, and silicate-substituted tricalcium phosphate.

12. The biomaterial as claimed in claim 7 wherein the biomaterial is an unmineralised porous patch comprising a non-porous collagen membrane bonded to a porous collagen-based material comprising collagen and a glycosaminoglycan.

13. An implant comprising a fabricated biomaterial as claimed in claim 7.

14. An implant as claimed in claim 13, further comprising cells.

15. A method of treatment of a defect in a target tissue of a patient comprising taking an implant as claimed in claim 13 and inserting the implant into the defect site of the patient.

16. A method as claimed in claim 15 wherein the target tissue is selected from the group consisting of: cartilage, bone, ligament, tendon, artery, Sharpey's fibres, meniscus, periodontal tissue, dentine, enamel, intervertebral discs, annulus fibrosus, and nucleus pulposus.

17. A method as claimed in claim 15 wherein the biomaterial is fixed at the defect site by a fixing means.

18. A method as claimed in claim 17 wherein the fixing means is selected from sutures, tacks, darts, polymeric tabs, bioadhesives, fibrin glue, fibrin clot forming means, adhesives from autologous body fluids and composites comprising one or more of the fixing means.

19. An implant as claimed in claim 13 for the treatment of a meniscal defect or as an arterial closure device.

20. The biomaterial as claimed in claim 7 wherein the collagen is present in the biomaterial in an amount of from 5 to 90 (dry) weight %.

21. A kit of parts comprising an implant as claimed in claim 13, in combination with a delivery device.

22. A method of fabricating a biomaterial, wherein the fabricated biomaterial produced comprises porous and non-porous collagen-based materials bonded with a bonding layer of dried gel, wherein the dried gel of the bonding layer comprises cross-linked collagens, wherein the method comprises:
   a) joining a porous collagen-based material to a non-porous collagen-based material using a bonding layer of a collagen gel, and
   b) drying the collagen gel to bond the porous and non-porous collagen-based materials together; and
   c) cross-linking the collagens in the bonding layer.

23. A process as claimed in claim 1, wherein the gel comprises from 0.1 to 2% of collagen weight/volume".

* * * * *